United States Patent [19]
Bird et al.

[11] Patent Number: 5,886,164
[45] Date of Patent: Mar. 23, 1999

[54] DNA ENCODING ENZYMES RELATED TO ETHYLENE BIOSYNTHESIS AND RIPENING FROM BANANA

[75] Inventors: Colin Roger Bird, Bracknell; Jonathon David Fletcher, Maidenhead, both of United Kingdom

[73] Assignee: Zeneca Limited, London, England

[21] Appl. No.: 632,598

[22] Filed: Apr. 15, 1996

[51] Int. Cl.$^6$ .............................. C07H 21/04; C12N 15/63
[52] U.S. Cl. .................... 536/23.2; 435/320.1; 536/23.6; 536/24.5
[58] Field of Search .................................. 536/23.2, 23.6, 536/24.1, 24.5; 435/320.1, 172.3, 419; 800/205, DIG. 9, DIG. 52, DIG. 65

[56] References Cited

FOREIGN PATENT DOCUMENTS

91/08299  6/1991  WIPO .

OTHER PUBLICATIONS

Hamilton AJ, et al. "Antisense gene that inhibits synthesis of the hormone ethylene in transgenic plants." Nature 346: 284–287, Jul. 19, 1990.

Oeller PW, et al. "Reversible inhibition of tomato fruit senescence by antisense RNA." Science 254: 437–439, Oct. 18, 1991.

Koziel MG, et al. "Optimizing expression of transgenes with an emphasis on post–transcriptional events." Plant Mol. Biol. 32: 393–405, 1996.

Stam M, et al. "The silence of genes in transgenic plants." Ann. Bot. 79: 3–12, 1997.

Smith CJS, et al. "Antisense RNA inhibition of polygalacturonase gene expression in transgenic tomatoes." Nature 334: 724–726, 1988.

May GD, et al. Generation of transgenic banana (Musa acuminata) plants via Agrobacterium–mediated transformation. Biotechnology 13: 486–492, May 3, 1995.

Smith, C. J. S., et al., Nature, "Antisense RNA inhibition of polygalacturonase gene expression in transgenic tomatoes", vol. 334, 1988, pp. 724–726.

Bevan, M., Nucleic Acids Research, "Binary *Agrobacterium* vectors for plant transformation", vol. 12, No. 22, 1984, pp. 8711–8721.

Bird, C. R., et al., Biotechnology and Genetic Engineering Reviews, "Manipulation of Plant Gene Expression by Antisense RNA", vol. 9, 1991, pp. 207–227.

Gray, J., et al., Plant Molecular Biology, "Molecular biology of fruit ripening and its manipulation with antisense genes", vol. 19, 1992, pp. 69–87.

May, G. D., et al., Biotechnology, "Generation of Transgenic Banana (*Musa acuminata*) Plants via *Agrobacterium*–Mediated Transformation", vol. 13, 1995, pp. 486–492.

*Primary Examiner*—Douglas W. Robinson
*Assistant Examiner*—Amy J. Nelson
*Attorney, Agent, or Firm*—Liza D. Hohenschutz

[57] ABSTRACT

A method of modifying ethylene biosynthesis in a plant comprises inserting into the genome of the said plant a DNA sequence such as SEQ-ID-NO-1 (encoding 1-aminocyclopropane-1-carboxylic acid synthase (ACS)) and/or sequence SEQ-ID-NO-2 (encoding an ethylene-forming enzyme (EFE)) which modifies the activity of at least one of ACS or EFE. The method may be used to modify fruit ripening characteristics, especially in bananas.

4 Claims, No Drawings

5,886,164

SEQUENCE LISTING ( 1 ) GENERAL INFORMATION:

( i i i ) NUMBER OF SEQUENCES: 50

( 2 ) INFORMATION FOR SEQ ID NO:1:

( i ) SEQUENCE CHARACTERISTICS:
        ( A ) LENGTH: 1712 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: MUSA ( v i i ) IMMEDIATE SOURCE:
        ( B ) CLONE: ACS GENE ( x i ) SEQUENCE DESCRIPTION: SEQ ID NO:1:

```
AAAACCTACA CACCGGGTCA CATGAGGATC TACGGCGAGG AGCACCCAAA TCAGCAGATC     60
CTCTCTCGGA TCGCGACCAA CGACGGCCAT GGCGAGAACT CCTCCTACTT CGATGGCTGG    120
AAGGCCTACG AGAAGGATCC TTTCCACCTC ACCGACAACC CCACGGGGGT CATCCAAATG    180
GGACTCGCAG AAAACCAGCT TTCCCTCGAC TTGATCCGAG ACTGGATGAA GAAGAACCCA    240
CAGGCTTCGA TCTGCACCGA AGAAGGGGTC TCAGAGTTCA AAGCAATTGC CAACTTTCAG    300
GACTATCATG GCCTCCCAAC CTTCCGAAAG GCCATCGCCC AGTTCATGGA GAAGGTGAGA    360
GGGGGACGAG CCAGATTTGA CCCAGACCGC ATCGTGATGA GCGGTGGAGC CACCGGCGCT    420
CAGGAAACCA TCGCCTTTTG CCTGGCTGAT CCTGGCGAGG CCTTCTTGAT TCCAACGCCA    480
TATTATCCGG GATTCGATCG AGACTTCAGG TGGAGGACAG GAGTTCAGCT CCTCCCCATT    540
CACTGCCACA GTTCCAACAA GTTCAAGATC ACCCTTGCCG CACTGGAGAC TGCTTACAGG    600
AAGGCTCGAA ACTCACACAT TAGAGTCAAA GGAATACTGG TGACCAACCC ATCGAACCCT    660
CTGGGCACAA CCATGGACAG AGAGACGCTG AGAACCCTAG TCAGCTTCGT CAACGAGAAA    720
AGGATGCACT TGGTGTGCGA CGAGATCTTC TCCGGAACCG TCTTCGACAA GCCGAGTTAC    780
GTGAGCGTCT CCGAGGTGAT CGAAGACGAG CCCTACTGCG ACAGGGATCT GATTCACATC    840
GCCTACAGCC TCTCCAAGGA CCTGGGCGTC CCTGGCTTCC GCGTCGGCGT CATATACTCC    900
TACAACGACG CCGTGGTCAG CTGCGCGAGG AAGATGTCGA GCTTTGGACT GGTCTCGTCG    960
CAGACGCAGC TCCTGCTCGC TTCCATGTTG GGAGACGAGG AGTTCACCAC GAGTTTCTTA   1020
GCGACGAGCC GGACGAGGTT GTGCGGGCGG CGCAGGGTCT TTACGGACGG CCTCAAGCGA   1080
GTCGGGATTC ATTGCTTGGA CGGCAACGCG GGGCTGTTCT GCTGGATGGA CTTGAGGCCG   1140
TTGCTGAAGG AAGCGACGGT GGAGGCGGAC GTCCGGCTGT GGCGGGTGAT CATCAACGAC   1200
GTGAAGCTCA ACATCTCGCC GGGGTCGTCC TTCCACTGCT CGGAGCCGGG GTGGTTCAGG   1260
GTGTGCTTCG CCAACATGGA CGACACGGCC ATGAAGATAG CGCTGAGGAG GATCGAGAGT   1320
TTCGTGTACC GGGAGAACGA CGCCGCTGTG CAGGCGAAGA ACAAGAGGAG GTGGGACGAA   1380
GCGCTGCGGC TGAGCTTGCC TCGTCGGAGG TTCGAGGATC CGTCCATCAT GACACCACAT   1440
CTGATGTCTC CCCACTCGCC TCTCGTTCAA GCCGCCACCT GAAACATCGA CAGCGGCGTG   1500
TCTGATGTCA AAGAAGGTTA ATTACCGTCT GATATGTTGC ACATTTCTTT GTTCTTTGGA   1560
TTATTTATTT TTTTTTTTGG GAAAAATGGG TTGAATGTTC CCACTAAGTT ATATTAGATT   1620
```

-continued

| | | | | | | |
|---|---|---|---|---|---|---|
| GTTATTCGGT | CTCATTCATG | TTATAGGAAA | CGAGGATAGA | ATTGCTTGCC | TCTCTCTTTC | 1680 |
| TTTTATATAT | GGAAATATGT | TGCAATTGGC | CT | | | 1712 |

(2) INFORMATION FOR SEQ ID NO:2:

(i) SEQUENCE CHARACTERISTICS:
        (A) LENGTH: 1181 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: MUSA (vii) IMMEDIATE SOURCE:
        (B) CLONE: EFE GENE (xi) SEQUENCE DESCRIPTION: SEQ ID NO:2:

| | | | | | | |
|---|---|---|---|---|---|---|
| AAAACCACAC | ACCACAAGTG | CAATCAGGGA | AGAAAGAGCG | TGTCATGGAT | TCCTTTCGG | 60 |
| TTATCGACAT | GGAGAAGCTT | TTGGGAAGGG | AGAGAGGAGC | AGCCATGGAG | ATCCTCCGAG | 120 |
| ATGCTTGCGA | GAAATGGGGC | TTCTTTGAGA | TTTTAAACCA | TGGCATCTCA | CATGACCTCA | 180 |
| TGGATGAAGT | GGAGAAGGTG | AACAAAGAAC | AGTACAACAA | ATGCAGGGAG | CAAAAGTTCA | 240 |
| ACGAGTTCGC | CAACAAAGCA | CTGGAAAACG | CCGACTCAGA | AATCGACCAC | CTCGACTGGG | 300 |
| AAAGCACCTT | TTTCCTGCGT | CATCTCCCCG | TCTCCAACAT | TTCTGAGATC | CCCGATCTTG | 360 |
| ATGACCAGTA | TAGGAAGGCG | ATGAAGGAAT | TTGCTGCAGC | GATAGAGAAG | CTGGCAGAGC | 420 |
| GGCTGCTCGA | CTTGCTGGGT | GAGAACCTGG | AGCTGGAGAA | GGGGTACCTG | AAGAAAGCCT | 480 |
| TCTCTAATGG | ATCCAAGGGG | CCAACCTTTG | GACCAAGGT | CAGCAGCTAC | CCACCATGCC | 540 |
| CACGCCCGGA | CCTGGTGAAG | GGCCTGAGGG | CGCACACCGA | CGCCGGAGGC | ATCATCTTGC | 600 |
| TCTTCCAGGA | CGACCAGGTC | AGCGGCCTGC | AGTTCCTCAA | GGACGGCGAG | TGGCTGGACG | 660 |
| TGCCCCCCAT | GCGCCATGCC | ATCGTCGTCA | ACCTCGGCGA | CCAGCTCGAG | GTAATCACCA | 720 |
| ATGGCAAGTA | CAAGAGCGTG | GTGCACCGCG | TGGTGGCTCA | GACTGATGGC | AACAGGATGT | 780 |
| CGATTGCCTC | CTTCTACAAC | CCCGGGAGCG | ACGCTGTGAT | CTTCCCGGCC | CCCGCTCTTG | 840 |
| TGGAGAAGGA | AGCGGAGGAG | AAGAAGGAGG | TCTATCCGAG | GTTCGTGTTC | GAGGATTACA | 900 |
| TGAAGCTCTA | CGTCGGGCAT | AAGTTCCAGG | CCAAGGAGCC | AAGATTCGAA | GCCATGAAAG | 960 |
| CCATGGAAGC | AGTTGCCACC | CACCCAATCG | CTACCTCTTA | AGTGACAGCC | CCCAAGTTAG | 1020 |
| TGCATGTCGC | TGTACTTCGC | GTTAGGAAGC | TGTCGTCTAT | GTCTATGTAA | CCCGATGGAA | 1080 |
| GCGTGGTATG | TACGTGTTTG | AGCCTTTTCT | AATGAAGCAA | GTCATATAAT | ATATATATAT | 1140 |
| ATATATATAT | ATATATATAT | ATATATAAAT | AATTACTCTT | C | | 1181 |

(2) INFORMATION FOR SEQ ID NO:3:

(i) SEQUENCE CHARACTERISTICS:
        (A) LENGTH: 7 amino acids
        (B) TYPE: amino acid
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: 5'PRIMER (xi) SEQUENCE DESCRIPTION: SEQ ID NO:3:

Phe Gln Asp Tyr His Gly Leu
1               5

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: LYCOPERSICON ESCULENTUM ( v i i ) IMMEDIATE SOURCE:
        ( B ) CLONE: OLIGONUCLEOTIDE PROBE 5'PRIMER ( x i ) SEQUENCE DESCRIPTION: SEQ ID NO:4:

TTTCAAGATT ATCATGGCTT G    21

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: SQUASH ( v i i ) IMMEDIATE SOURCE:
        ( B ) CLONE: OLIGONUCLEOTIDE PROBE 5'PRIMER ( x i ) SEQUENCE DESCRIPTION: SEQ ID NO:5:

TTTCAAGATT ACCATGGCTT A    21

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: MUNG BEAN ( v i i ) IMMEDIATE SOURCE:
        ( B ) CLONE: OLIGONUCLEOTIDE PROBE 5'PRIMER ( x i ) SEQUENCE DESCRIPTION: SEQ ID NO:6:

TTTCAGGATT ACCATGGTCT G    21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: TOBACCO ( v i i ) IMMEDIATE SOURCE:
   ( B ) CLONE: OLIGONUCLEOTIDE PROBE 5'PRIMER ( x i ) SEQUENCE DESCRIPTION: SEQ ID NO:7:

TTTCAAGATT ATCACGGCCT A    21

( 2 ) INFORMATION FOR SEQ ID NO:8:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: cDNA ( v i ) ORIGINAL SOURCE:
   ( A ) ORGANISM: CARNATION ( v i i ) IMMEDIATE SOURCE:
   ( B ) CLONE: OLIGONUCLEOTIDE PROBE ( x i ) SEQUENCE DESCRIPTION: SEQ ID NO:8:

TTTCAGGATT ATCATGGTTT G    21

( 2 ) INFORMATION FOR SEQ ID NO:9:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: cDNA ( v i ) ORIGINAL SOURCE:
   ( A ) ORGANISM: MOTH ORCHID ( v i i ) IMMEDIATE SOURCE:
   ( B ) CLONE: OLIGONUCLEOTIDE PROBE 5'PRIMER ( x i ) SEQUENCE DESCRIPTION: SEQ ID NO:9:

TTTCAGGACT ATCATGGCCT C    21

( 2 ) INFORMATION FOR SEQ ID NO:10:

( i ) SEQUENCE CHARACTERISTICS:
   ( A ) LENGTH: 21 base pairs
   ( B ) TYPE: nucleic acid
   ( C ) STRANDEDNESS: single
   ( D ) TOPOLOGY: linear ( i i ) MOLECULE TYPE: cDNA ( v i i ) IMMEDIATE SOURCE:
   ( B ) CLONE: DEGENERATE OLIGONUCLEOTIDE PROBE ( x i ) SEQUENCE DESCRIPTION: SEQ ID NO:10:

TTTCARGAYT AYCAYGGY YT G    21

( 2 ) INFORMATION FOR SEQ ID NO:11:

( i ) SEQUENCE CHARACTERISTICS:
   ( A ) LENGTH: 7 amino acids
   ( B ) TYPE: amino acid
   ( D ) TOPOLOGY: unknown ( i i ) MOLECULE TYPE: peptide ( v i ) ORIGINAL SOURCE:
   ( A ) ORGANISM: LYCOPERSICON ESCULENTUM ( v i i ) IMMEDIATE SOURCE:
   ( B ) CLONE: PROBE 3'PRIMER ( x i ) SEQUENCE DESCRIPTION: SEQ ID NO:11:

Pro Ser Asn Pro Leu Gly Thr
1                5

( 2 ) INFORMATION FOR SEQ ID NO:12:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: LYCOPERSICON ESCULENTUM ( v i i ) IMMEDIATE SOURCE:
      ( B ) CLONE: OLIGONUCLEOTIDE PROBE 3'PRIMER ( x i ) SEQUENCE DESCRIPTION: SEQ ID NO:12:

CCATCAAATC CATTGGGCAC C                                                                 21

( 2 ) INFORMATION FOR SEQ ID NO:13:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: SQUASH ( v i i ) IMMEDIATE SOURCE:
      ( B ) CLONE: OLIGONUCLEOTIDE PROBE 3'PRIMER ( x i ) SEQUENCE DESCRIPTION: SEQ ID NO:13:

CCCTCAAATC CCTTAGGCAC A                                                                 21

( 2 ) INFORMATION FOR SEQ ID NO:14:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
      ( A ) ORGANISM: MUNG BEAN ( v i i ) IMMEDIATE SOURCE:
      ( B ) CLONE: OLGIONUCLEOTIDE PROBE 3'PRIMER ( x i ) SEQUENCE DESCRIPTION: SEQ ID NO:14:

CCATCAAATC CATTAGGCAC A                                                                 21

( 2 ) INFORMATION FOR SEQ ID NO:15:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: cDNA ( v i ) ORIGINAL SOURCE:
    ( A ) ORGANISM: TOBACCO ( v i i ) IMMEDIATE SOURCE:
    ( B ) CLONE: OLIGONUCLEOTIDE PROBE 3'PRIMER ( x i ) SEQUENCE DESCRIPTION: SEQ ID NO:15:

```
CCATCAAATC CATTAGGCAC C                                                         21
```

( 2 ) INFORMATION FOR SEQ ID NO:16:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: MOTH ORCHID ( v i i ) IMMEDIATE SOURCE:
        ( B ) CLONE: OLIGONUCLEOTIDE PROBE 3'PRIMER ( x i ) SEQUENCE DESCRIPTION: SEQ ID NO:16:

```
CCTTCGAATC CTCTGGGCAC C                                                         21
```

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: DEGENERATE OLIGONUCLEOTIDE PROBE ( x i ) SEQUENCE DESCRIPTION: SEQ ID NO:17:

```
BGTKCCYARD GGATTTSABG G                                                         21
```

( 2 ) INFORMATION FOR SEQ ID NO:18:

( i ) SEQUENCE CHARACTERISTICS:
        ( A ) LENGTH: 211 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: BANANA ( v i i ) IMMEDIATE SOURCE:
        ( B ) CLONE: pBASH14

( x i ) SEQUENCE DESCRIPTION: SEQ ID NO:18:

```
TTTCAGGACT ACCATGGTCT GCCGGACTTC CGTAAGTAAT CACCGTCTGC ATCCATAATG               60
CAGCTCCTCG ATCCTTACGC ATGCGTGCCA TGAACGATGA GGGCACAGTT GGATCGATAT              120
GCGTTGCTAT AGCCGAAAGT AATGACGCGA TCATCTATGG AAATGCACAG GCCATTGCCA              180
AGTTCATGGA GAAAGCGAGA GGAGGACGAG C                                             211
```

(2) INFORMATION FOR SEQ ID NO:19:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: BANANA (vii) IMMEDIATE SOURCE:
        (B) CLONE: TRANSLATION OF pBASH14

(xi) SEQUENCE DESCRIPTION: SEQ ID NO:19:

```
Phe Gln Asp Tyr His Gly Leu Pro Asp Phe Arg Lys
 1               5                  10
```

(2) INFORMATION FOR SEQ ID NO:20:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: TOMACC1

(xi) SEQUENCE DESCRIPTION: SEQ ID NO:20:

```
Phe Gln Asp Tyr His Gly Leu Pro Glu Phe Arg Lys
 1               5                  10
```

(2) INFORMATION FOR SEQ ID NO:21:

(i) SEQUENCE CHARACTERISTICS:
        (A) LENGTH: 12 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: TOMACC2

(xi) SEQUENCE DESCRIPTION: SEQ ID NO:21:

```
Phe Gln Asp Tyr His Gly Leu Pro Glu Phe Thr Asn
 1               5                  10
```

(2) INFORMATION FOR SEQ ID NO:22:

(i) SEQUENCE CHARACTERISTICS:
        (A) LENGTH: 13 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: BANANA (vii) IMMEDIATE SOURCE:

(B) CLONE: TRANSLATION OF pBASH14

(x i) SEQUENCE DESCRIPTION: SEQ ID NO:22:

Ala Ile Ala Lys Phe Met Glu Lys Ala Arg Gly Gly Arg
1               5                       10

(2) INFORMATION FOR SEQ ID NO:23:

(i) SEQUENCE CHARACTERISTICS:
        (A) LENGTH: 13 amino acids
        (B) TYPE: amino acid
        (C) STRANDEDNESS: single
        (D) TOPOLOGY: unknown (i i) MOLECULE TYPE: peptide (v i) ORIGINAL SOURCE:
        (A) ORGANISM: LYCOPERSICON ESCULENTUM (v i i) IMMEDIATE SOURCE:
        (B) CLONE: TOMACC1

(x i) SEQUENCE DESCRIPTION: SEQ ID NO:23:

Ala Ile Ala Lys Phe Met Glu Lys Thr Arg Gly Gly Arg
1               5                       10

(2) INFORMATION FOR SEQ ID NO:24:

(i) SEQUENCE CHARACTERISTICS:
        (A) LENGTH: 13 amino acids
        (B) TYPE: amino acid
        (C) STRANDEDNESS: single
        (D) TOPOLOGY: unknown (i i) MOLECULE TYPE: peptide (v i) ORIGINAL SOURCE:
        (A) ORGANISM: LYCOPERSICON ESCULENTUM (v i i) IMMEDIATE SOURCE:
        (B) CLONE: TOMACC2

(x i) SEQUENCE DESCRIPTION: SEQ ID NO:24:

Ala Ile Ala Lys Phe Met Glu Lys Thr Arg Gly Gly Lys
1               5                       10

(2) INFORMATION FOR SEQ ID NO:25:

(i) SEQUENCE CHARACTERISTICS:
        (A) LENGTH: 7 amino acids
        (B) TYPE: amino acid
        (C) STRANDEDNESS: single
        (D) TOPOLOGY: unknown (i i) MOLECULE TYPE: peptide (v i i) IMMEDIATE SOURCE:
        (B) CLONE: 5'PRIMER (x i) SEQUENCE DESCRIPTION: SEQ ID NO:25:

Asp Trp Glu Ser Thr Phe Phe
1               5

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: cDNA ( v i ) ORIGINAL SOURCE:
  ( A ) ORGANISM: LYCOPERSICON ESCULTENTUM ( v i i ) IMMEDIATE SOURCE:
  ( B ) CLONE: 5'PRIMER ( x i ) SEQUENCE DESCRIPTION: SEQ ID NO:26:

GATTGGGAAA GCACTTTCTT C  21

( 2 ) INFORMATION FOR SEQ ID NO:27:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: MELON ( v i i ) IMMEDIATE SOURCE:
    ( B ) CLONE: 5'PRIMER ( x i ) SEQUENCE DESCRIPTION: SEQ ID NO:27:

GACTGGGAAA GCACTTTTTT T  21

( 2 ) INFORMATION FOR SEQ ID NO:28:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: PEACH ( v i i ) IMMEDIATE SOURCE:
    ( B ) CLONE: 3'PRIMER ( x i ) SEQUENCE DESCRIPTION: SEQ ID NO:28:

GACTGGGAAA GCACCTTCTA C  21

( 2 ) INFORMATION FOR SEQ ID NO:29:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: AVOCADO ( v i i ) IMMEDIATE SOURCE:
    ( B ) CLONE: 5'PRIMER ( x i ) SEQUENCE DESCRIPTION: SEQ ID NO:29:

GACTGGGAGA GCACCTTCTT C  21

( 2 ) INFORMATION FOR SEQ ID NO:30:

( i ) SEQUENCE CHARACTERISTICS:
    ( A ) LENGTH: 21 base pairs
    ( B ) TYPE: nucleic acid (C) STRANDEDNESS: single
        (D) TOPOLOGY: linear (ii) MOLECULE TYPE: cDNA (vi) ORIGINAL SOURCE:
        (A) ORGANISM: MUSTARD (vii) IMMEDIATE SOURCE:
        (B) CLONE: 5'PRIMER (xi) SEQUENCE DESCRIPTION: SEQ ID NO:30:

GATTGGGAAA GCACTTTCTA C                                                    21

(2) INFORMATION FOR SEQ ID NO:31:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: APPLE (vii) IMMEDIATE SOURCE:
        (B) CLONE: 5'PRIMER (xi) SEQUENCE DESCRIPTION: SEQ ID NO:31:

GACTGGGAAA GCACCTTCTT C                                                    21

(2) INFORMATION FOR SEQ ID NO:32:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: CARNATION (vii) IMMEDIATE SOURCE:
        (B) CLONE: 5'PRIMER (xi) SEQUENCE DESCRIPTION: SEQ ID NO:32:

GATTGGGAGA GCACCTTCTA C                                                    21

(2) INFORMATION FOR SEQ ID NO:33:

(i) SEQUENCE CHARACTERISTICS:
        (A) LENGTH: 19 base pairs
        (B) TYPE: nucleic acid
        (C) STRANDEDNESS: single
        (D) TOPOLOGY: unknown (ii) MOLECULE TYPE: peptide (vii) IMMEDIATE SOURCE:
        (B) CLONE: DEGENERATE OLIGONUCLEOTIDE PROBE 5'

(xi) SEQUENCE DESCRIPTION: SEQ ID NO:33:

GAYTGGGARA GCACYTTYT                                                       19

(2) INFORMATION FOR SEQ ID NO:34:

(i) SEQUENCE CHARACTERISTICS:
        (A) LENGTH: 7 amino acids (B) TYPE: amino acid
              (C) STRANDEDNESS: single
              (D) TOPOLOGY: unknown (ii) MOLECULE TYPE: peptide (vi) ORIGINAL SOURCE:
              (A) ORGANISM: LYCOPERSICON ESCULENTUM (vii) IMMEDIATE SOURCE:
              (B) CLONE: 3'PRIMER (xi) SEQUENCE DESCRIPTION: SEQ ID NO:34:

Val  Ser  Asn  Tyr  Pro  Pro  Cys
     1                   5

(2) INFORMATION FOR SEQ ID NO:35:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: LYCOPERSICON ESCULENTUM (vii) IMMEDIATE SOURCE:
              (B) CLONE: 3'PRIMER (xi) SEQUENCE DESCRIPTION: SEQ ID NO:35:

GTTAGCAACT ATCCACCATG T                    21

(2) INFORMATION FOR SEQ ID NO:36:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: PEACH (vii) IMMEDIATE SOURCE:
              (B) CLONE: 3'PRIMER (xi) SEQUENCE DESCRIPTION: SEQ ID NO:36:

GTTAGCAACT ACCCTCCTTG T                    21

(2) INFORMATION FOR SEQ ID NO:37:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: cDNA (vi) ORIGINAL SOURCE:
              (A) ORGANISM: APPLE (vii) IMMEDIATE SOURCE:
              (B) CLONE: 3'PRIMER (xi) SEQUENCE DESCRIPTION: SEQ ID NO:37:

GTCAGCAACT ACCCTCCATG C                    21

( 2 ) INFORMATION FOR SEQ ID NO:38:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: AVOCADO ( v i i ) IMMEDIATE SOURCE:
        ( B ) CLONE: 3'PRIMER ( x i ) SEQUENCE DESCRIPTION: SEQ ID NO:38:

GTCAGCAACT ACCCACCCTG C        21

( 2 ) INFORMATION FOR SEQ ID NO:39:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: MELON ( v i i ) IMMEDIATE SOURCE:
        ( B ) CLONE: 3'PRIMER ( x i ) SEQUENCE DESCRIPTION: SEQ ID NO:39:

GTTAGCAATT ACCCCCCATG T        21

( 2 ) INFORMATION FOR SEQ ID NO:40:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: MUSTARD ( v i i ) IMMEDIATE SOURCE:
        ( B ) CLONE: 3'PRIMER ( x i ) SEQUENCE DESCRIPTION: SEQ ID NO:40:

GTGAGCAACT ATCCAGCTTG T        21

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( v i i ) IMMEDIATE SOURCE:
        ( B ) CLONE: DEGENERATE OLIGONUCLEOTIDE PROBE 3'

( x i ) SEQUENCE DESCRIPTION: SEQ ID NO:41:

RCADGGWGGR TARTTGCTVA C        21

( 2 ) INFORMATION FOR SEQ ID NO:42:

( i ) SEQUENCE CHARACTERISTICS:
    ( A ) LENGTH: 331 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: BANANA ( v i i ) IMMEDIATE SOURCE:
    ( B ) CLONE: pBEAR13

( x i ) SEQUENCE DESCRIPTION: SEQ ID NO:42:

```
GGGAGAGCAC CTTTTTCCTG CGTCATCTCC CCGTCTCCAA CATTTCTGAG ATCCCCGATC      60
TTGATGACCA GTATAGGTTG CACGATCTGA TCATGATGTC ATCTTCTAGC CTTGTCTTTT     120
CACCTTGCTC ATCGTTTCGT TTCTTGGGAC GATGACTGCG TGCAGGAAGG CGATGAAGGA     180
ATTTGCTGCA GCGATAGAGA AGCTGGCAGA GCGGCTGCTC GACTTGCTGG GTGAGAACCT     240
GGAGCTGGAG AAGGGGCTCC TGAAGAAGGC CTTCTCTAAT GGATCCAAGG GGCCAACCTT     300
TGGGACCAAG GTCAGCAACT ACCCACCTTG C                                    331
```

( 2 ) INFORMATION FOR SEQ ID NO:43:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: unknown ( i i ) MOLECULE TYPE: peptide ( v i ) ORIGINAL SOURCE:
    ( A ) ORGANISM: BANANA ( v i i ) IMMEDIATE SOURCE:
    ( B ) CLONE: TRANSLATION OF pBEAR13

( x i ) SEQUENCE DESCRIPTION: SEQ ID NO:43:

```
Glu  Ser  Thr  Phe  Phe  Leu  Arg  His  Leu  Pro  Val  Ser  Asn  Ile  Ser  Glu
1                  5                            10                           15

Ile  Pro  Asp  Leu  Asp  Asp  Gln  Tyr  Arg
               20                      25
```

( 2 ) INFORMATION FOR SEQ ID NO:44:

( i ) SEQUENCE CHARACTERISTICS:
    ( A ) LENGTH: 25 amino acids
    ( B ) TYPE: amino acid
    ( C ) STRANDEDNESS: single
    ( D ) TOPOLOGY: unknown ( i i ) MOLECULE TYPE: peptide ( v i ) ORIGINAL SOURCE:
    ( A ) ORGANISM: LYCOPERSICON ESCULENTUM ( v i i ) IMMEDIATE SOURCE:
    ( B ) CLONE: ACO1

( x i ) SEQUENCE DESCRIPTION: SEQ ID NO:44:

```
Glu  Ser  Thr  Phe  Phe  Leu  Arg  His  Leu  Pro  Thr  Ser  Asn  Ile  Ser  Gln
1                  5                            10                           15

Val  Pro  Asp  Leu  Asp  Glu  Glu  Tyr  Arg
```

20                                  25

(2) INFORMATION FOR SEQ ID NO:45:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: ACO2

(xi) SEQUENCE DESCRIPTION: SEQ ID NO:45:

Glu Ser Thr Phe Phe Leu Arg His Leu Pro Ser Ser Asn Ile Ser Gln
1               5                   10                  15

Leu Pro Asp Leu Asp Asp Val Tyr Arg
            20              25

(2) INFORMATION FOR SEQ ID NO:46:

(i) SEQUENCE CHARACTERISTICS:
        (A) LENGTH: 25 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: ACO3

(xi) SEQUENCE DESCRIPTION: SEQ ID NO:46:

Glu Ser Thr Phe Phe Leu Arg His Leu Pro Thr Ser Asn Ile Ser Gln
1               5                   10                  15

Val Pro Asp Leu Asp Glu Glu Tyr Arg
            20              25

(2) INFORMATION FOR SEQ ID NO:47:

(i) SEQUENCE CHARACTERISTICS:
        (A) LENGTH: 55 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: BANANA (vii) IMMEDIATE SOURCE:
        (B) CLONE: TRANSLATION OF pBEAR13 after intron (xi) SEQUENCE DESCRIPTION: SEQ ID NO:47:

Lys Ala Met Lys Glu Phe Ala Ala Ala Ile Glu Lys Leu Ala Glu Arg
1               5                   10                  15

Leu Leu Asp Leu Leu Gly Glu Asn Leu Glu Leu Glu Lys Gly Leu Leu
            20                  25                  30

Lys Lys Ala Phe Ser Asn Gly Ser Lys Gly Pro Thr Phe Gly Thr Lys
        35                  40                  45

```
            Val  Ser  Asn  Tyr  Pro  Pro  Cys
                 50                  55
```

(2) INFORMATION FOR SEQ ID NO:48:

(i) SEQUENCE CHARACTERISTICS:
        (A) LENGTH: 54 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: ACO1 AFTER INTRON (xi) SEQUENCE DESCRIPTION: SEQ ID NO:48:

```
Glu  Val  Met  Arg  Asp  Phe  Ala  Lys  Arg  Leu  Glu  Lys  Leu  Ala  Glu  Glu
1                   5                        10                       15

Leu  Leu  Asp  Leu  Leu  Cys  Glu  Asn  Leu  Gly  Leu  Glu  Lys  Gly  Tyr  Leu
               20                       25                       30

Lys  Asn  Ala  Phe  Tyr  Gly  Ser  Lys  Gly  Pro  Asn  Phe  Gly  Thr  Lys  Val
          35                       40                       45

Ser  Asn  Tyr  Pro  Pro  Cys
     50
```

(2) INFORMATION FOR SEQ ID NO:49:

(i) SEQUENCE CHARACTERISTICS:
        (A) LENGTH: 53 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:
        (B) CLONE: ACO2 AFTER INTRON (xi) SEQUENCE DESCRIPTION: SEQ ID NO:49:

```
Val  Met  Arg  Asp  Phe  Arg  Lys  Arg  Leu  Glu  Lys  Leu  Ala  Glu  Glu  Leu
1                   5                        10                       15

Leu  Asp  Leu  Leu  Cys  Glu  Asn  Leu  Gly  Leu  Glu  Lys  Ser  Tyr  Leu  Lys
               20                       25                       30

Asn  Thr  Phe  Tyr  Gly  Ser  Lys  Gly  Pro  Asn  Phe  Gly  Thr  Lys  Val  Ser
          35                       40                       45

Asn  Tyr  Pro  Pro  Cys
     50
```

(2) INFORMATION FOR SEQ ID NO:50:

(i) SEQUENCE CHARACTERISTICS:
        (A) LENGTH: 54 amino acids
        (B) TYPE: amino acid
        (C) STRANDEDNESS: single
        (D) TOPOLOGY: unknown (ii) MOLECULE TYPE: peptide (vi) ORIGINAL SOURCE:
        (A) ORGANISM: LYCOPERSICON ESCULENTUM (vii) IMMEDIATE SOURCE:

(B) CLONE: ACO3 AFTER INTRON (xi) SEQUENCE DESCRIPTION: SEQ ID NO:50:

| Glu | Val | Met | Arg | Asp | Phe | Ala | Lys | Arg | Leu | Glu | Lys | Leu | Ala | Glu | Glu |
|---|---|---|---|---|---|---|---|---|---|---|---|---|---|---|---|
| 1 | | | | 5 | | | | | 10 | | | | | 15 | |

| Leu | Leu | Asp | Leu | Leu | Cys | Glu | Asn | Leu | Gly | Leu | Glu | Lys | Gly | Tyr | Leu |
|---|---|---|---|---|---|---|---|---|---|---|---|---|---|---|---|
| | | | 20 | | | | | 25 | | | | | 30 | | |

| Lys | Asn | Ala | Phe | Tyr | Gly | Ser | Lys | Gly | Pro | Asn | Phe | Gly | Thr | Lys | Val |
|---|---|---|---|---|---|---|---|---|---|---|---|---|---|---|---|
| | | 35 | | | | | 40 | | | | | 45 | | | |

| Ser | Asn | Tyr | Pro | Pro | Cys |
|---|---|---|---|---|---|
| | 50 | | | | |

DNA ENCODING ENZYMES RELATED TO ETHYLENE BIOSYNTHESIS AND RIPENING FROM BANANA

BACKGROUND OF THE INVENTION

This application relates to DNAs, isolated from banana (Musa), DNA constructs containing the banana DNA, plant cells containing the constructs and plants derived therefrom. In particular it involves the use of antisense or sense RNA technology to control gene expression in plants.

Many physiological and developmental processes are controlled by ethylene in higher plants, including banana (Genus: Musa). These processes include fruit ripening where ethylene may be involved in both the initiation and rate of continuation of many of the changes involved in fruit ripening. However the exact role of ethylene has hitherto not been fully understood. We have now isolated a DNA involved in the generation of ethylene in bananas. In this invention, we provide such DNA, and methods of using it. One such use is a method for controlling the rate of production of ethylene in ripening bananas. In this way the rate of many of the ethylene-related changes associated with fruit ripening on a plant can be modified to obtain desired ripening characteristics.

The modification of plant gene expression has been achieved by several methods. The molecular biologist can choose from a range of known methods to decrease or increase gene expression or to alter the spatial or temporal expression of a particular gene. For example, the expression of either specific antisense RNA or partial (truncated) sense RNA has been utilised to reduce the expression of various target genes in plants (as reviewed by Bird and Ray, 1991, Biotechnology and Genetic Engineering Reviews 9:207–227). These techniques involve the incorporation into the genome of the plant of a synthetic gene designed to express either antisense or sense RNA. They have been successfully used to down-regulate the expression of a range of individual genes involved in the development and ripening of tomato fruit (Gray et al, 1992, Plant Molecular Biology, 19:69–87). Methods to increase the expression of a target gene have also been developed. For example, additional genes designed to express RNA containing the complete coding region of the target gene may be incorporated into the genome of the plant to "over-express" the gene product. Various other methods to modify gene expression are known; for example, the use of alternative regulatory sequences.

An object of the present invention is to provide new materials for use in the genetic control of ethylene biosynthesis in fruit, and hence ethylene-induced processes involved in fruit ripening, particularly banana fruit.

BRIEF SUMMARY OF THE INVENTION

According to a first aspect of the present invention, there is provided a method of modifying ethylene biosynthesis in a plant comprising inserting into the genome of the said plant a DNA sequence which modifies the activity of at least one of ACS or EFE.

Preferably, the said ACS has the sequence SEQ-ID-NO-1 and the said EFE has the sequence SEQ-ID-NO-2.

In particular, the method may be used to modify fruit ripening characteristics, especially in bananas.

The levels of ethylene biosynthesis may be either reduced or increased during development and ripening depending on the ripening characteristics desired for the modified fruit.

"Antisense" or "partial sense" or other techniques may be used to reduce the expression of either ACS or EFE in developing and ripening fruit. The levels of ACS or EFE may also be increased; for example, by incorporation of additional ACS or EFE genes. The additional genes may be designed to give either the same or different spatial and temporal patterns of expression in the fruit.

The present invention provides clones of genes which express enzymes involved in ethylene biosynthesis: 1-aminocyclopropane-1-carboxylic acid synthase (ACS) and ethylene-forming enzyme (EFE). ACS and EFE are involved in ethylene production, and hence in the ripening of bananas. cDNA clones representing these genes have been cloned and characterised.

According to the present invention we provide cDNA clones representing at least part of genes derived from banana that encode either ACS or EFE. Example of such clones are clone pACS6 (ACS) and clone pACOS7 (EFE). We further provide DNA constructs comprising a DNA sequence homologous to some or all of genes derived from banana that encode either ACS or EFE, preceded by a transcriptional initiation region operative in plants, so that the construct can generate RNA in plant cells.

DETAILED DESCRIPTION OF THE INVENTION cDNA clones encoding a ACS and EFE have been obtained from a banana fruit pulp cDNA library. The clones are hereinafter called pACS6 (ACS) and pACOS7 (EFE). The full nucleotide sequence of the ACS cDNA (clone pACS6) is given as SEQ ID NO 1 and that of the EFE cDNA (clone pACOS7) is given as SEQ ID NO 2.

Applicant has deposited, under the provisions of the Budapest Treaty on the Deposit of Microorganisms for Patent Purposes, at the National Collection of Industrial & Marine Bacteria, Aberdeen, United Kingdom, cDNA libraries of ripening-related genes from banana fruit pulp and banana fruit peel. The Accession Numbers are NCIMB 40813 and 40814 and the date of deposit for both deposits is 9th Jul. 1996.

An alternative source of the DNA sequence is a suitable gene encoding either ACS or EFE. This gene may differ from the corresponding cDNA in that introns may be present. The introns are not transcribed into mRNA (or, if so transcribed, are subsequently cut out). Oligonucleotide probes or the cDNA clone may be used to isolate the actual ACS or EFE gene(s) by screening banana genomic DNA libraries. Such genomic clones may include control sequences operating in the plant genome. Thus it is also possible to isolate promoter sequences which may be used to drive expression of the enzymes or any other protein. These promoters may be particularly responsive to certain developmental events (such as ripening) and environmental conditions. Banana ACS or EFE gene promoters may be used to drive expression of any target gene.

ACS or EFE DNA sequence may be isolated from banana cDNA or genomic DNA libraries using oligonucleotide probes based on the pACS6 or pACOS7 sequences. A banana ACS DNA sequence is any sequence from banana which cross-hybridises with SEQ ID NO 1, preferably having at least 60% homology with SEQ ID NO 1. A banana ACS DNA sequence may encode a protein which is homologous to the predicted gene product encoded by SEQ ID NO 1. A banana EFE DNA sequence is any sequence from banana which cross-hybridises with SEQ ID NO 2, preferably having at least 60% homology with SEQ ID NO 2. A banana EFE DNA sequence may encode a protein which is homologous to the predicted gene product encoded by SEQ ID NO 2.

A further way of obtaining ACS and EFE DNA sequence is to synthesise it ab initio from the appropriate bases, for example using the appropriate cDNA sequence as a guide.

Some or all of the ACS or EFE sequences may be incorporated into DNA constructs suitable for plant transformation. These DNA constructs may then be used to modify ACS or EFE gene expression in plants. "Antisense" or "partial sense" or other techniques may be used to reduce ACS or EFE gene expression in plant tissue (down-regulation). The levels of expression may also be increased (up-regulation); for example, by incorporation of additional ACS or EFE genes. The additional genes may be designed to give either the same or different spatial and temporal patterns of expression in the plant.

According to a further aspect of the invention there is provided a DNA construct comprising some or all of a ACS or EFE DNA sequence under the control of a transcriptional initiation region operative in plants, so that the construct can generate RNA in plant cells.

The fruit ripening characteristics and related characteristics of plant parts may be modified by transformation with a DNA construct according to the invention. The invention also provides plant cells containing such constructs; plants derived therefrom having modified ACS or EFE gene expression; and seeds of such plants.

A DNA construct according to the invention may be an "antisense" construct generating "antisense" RNA or a "sense" construct (encoding at least part of the functional enzyme) generating "sense" RNA. "Antisense RNA" is an RNA sequence which is complementary to a sequence of bases in the corresponding mRNA: complementary in the sense that each base (or the majority of bases) in the antisense sequence (read in the 3' to 5' sense) is capable of pairing with the corresponding base (G with C, A with U) in the mRNA sequence read in the 5' to 3' sense. Such antisense RNA may be produced in the cell by transformation with an appropriate DNA construct arranged to generate a transcript with at least part of its sequence complementary to at least part of the coding strand of the relevant gene (or of a DNA sequence showing substantial homology therewith). "Sense RNA" is an RNA sequence which is substantially homologous to at least part of the corresponding mRNA sequence. Such sense RNA may be produced in the cell by transformation with an appropriate DNA construct arranged in the normal orientation so as to generate a transcript with a sequence identical to at least part of the coding strand of the relevant gene (or of a DNA sequence showing substantial homology therewith). Suitable sense constructs may be used to inhibit gene expression (as described in International Patent Publication WO91/08299) or a sense construct encoding and expressing the functional enzyme may be transformed into the plant to over-express the enzyme.

DNA constructs according to the invention may comprise a base sequence at least 10 bases (preferably at least 35 bases) in length for transcription into RNA. There is no theoretical upper limit to the base sequence—it may be as long as the relevant mRNA produced by the cell—but for convenience it will generally be found suitable to use sequences between 100 and 1000 bases in length. The preparation of such constructs is described in more detail below.

As a source of the DNA base sequence for transcription, a suitable cDNA or genomic DNA or synthetic polynucleotide may be used. The isolation of suitable ACS or EFE sequences is described above. Sequences coding for the whole, or substantially the whole, of either enzyme may thus be obtained. Suitable lengths of these DNA sequences may be cut out for use by means of restriction enzymes. When using genomic DNA as the source of a partial base sequence for transcription it is possible to use either intron or exon regions or a combination of both.

To obtain constructs suitable for modifying expression of ACS or EFE in plant cells, the cDNA sequence as found in the enzyme cDNA or the gene sequence as found in the chromosome of the plant may be used. Recombinant DNA constructs may be made using standard techniques. For example, the DNA sequence for transcription may be obtained by treating a vector containing said sequence with restriction enzymes to cut out the appropriate segment. The DNA sequence for transcription may also be generated by annealing and ligating synthetic oligonucleotides or by using synthetic oligonucleotides in a polymerase chain reaction (PCR) to give suitable restriction sites at each end. The DNA sequence is then cloned into a vector containing upstream promoter and downstream terminator sequences. If antisense DNA is required, the cloning is carried out so that the cut DNA sequence is inverted with respect to its orientation in the strand from which it was cut.

In a construct expressing antisense RNA, the strand that was formerly the template strand becomes the coding strand, and vice versa. The construct will thus encode RNA in a base sequence which is complementary to part or all of the sequence of the enzyme mRNA. Thus the two RNA strands are complementary not only in their base sequence but also in their orientations (5' to 3').

In a construct expressing sense RNA, the template and coding strands retain the assignments and orientations of the original plant gene. Constructs expressing sense RNA encode RNA with a base sequence which is homologous to part or all of the sequence of the mRNA. In constructs which express the functional enzyme, the whole of the coding region of the gene is linked to transcriptional control sequences capable of expression in plants.

For example, constructs according to the present invention may be made as follows. A suitable vector containing the desired base sequence for transcription (such as the pACS6 or pACOS7 cDNA clones) is treated with restriction enzymes to cut the sequence out. The DNA strand so obtained is cloned (if desired, in reverse orientation) into a second vector containing the desired promoter sequence and the desired terminator sequence. Suitable promoters include the 35S cauliflower mosaic virus promoter or developmentally regulated fruit promoters. Suitable terminator sequences include that of the *Agrobacterium tumefaciens* nopaline synthase gene (the nos 3' end).

In a DNA construct according to the invention, the transcriptional initiation region may be derived from any plant-operative promoter. The transcriptional initiation region may be positioned for transcription of a DNA sequence encoding RNA which is complementary to a substantial run of bases in a mRNA encoding the ACS or EFE enzyme (making the DNA construct a full or partial antisense construct).

The transcriptional initiation region (or promoter) operative in plants may be a constitutive promoter (such as the 35S cauliflower mosaic virus promoter) or an inducible or developmentally regulated promoter (such as fruit-specific promoters), as circumstances require. For example, it may be desirable to modify ACS or EFE activity only during fruit development and/or ripening. Use of a constitutive promoter will tend to affect enzyme levels and functions in all parts of the plant, while use of a tissue specific promoter allows more selective control of gene expression and affected functions (eg fruit coloration). Thus in applying the invention it may be found convenient to use a promoter that will give expression during fruit development and/or ripening. Thus the antisense or sense RNA is only produced in the organ in which its action is required.

The DNA constructs of the invention may be inserted into banana plants to regulate the expression of ACS or EFE genes and the production of ACS or EFE enzymes, resulting in modification of plant characteristics (in particular fruit-ripening). Depending on the nature of the construct, the production of the ACS or EFE may be increased, or reduced, either throughout or at particular stages in the life of the plant. Generally, as would be expected, production of the enzyme is enhanced only by constructs which express RNA homologous to the substantially complete endogenous enzyme mRNAs. Full-length sense constructs may also inhibit enzyme expression. Constructs containing an incomplete DNA sequence shorter than that corresponding to the complete gene generally inhibit the expression of the gene and production of the enzymes, whether they are arranged to express sense or antisense RNA. Full-length antisense constructs also inhibit gene expression.

A DNA construct of the invention is transformed into a target banana cell. The target banana cell may be part of a whole plant or may be an isolated cell or part of a tissue which may be regenerated into a whole plant. Plants may be derived from the transformed plant cell by regeneration of transformants and by production of successive clonal generations of the transformant.

Retardation of the rate of ripening will reduce the rate of deterioration of banana fruit after harvest. As a result of this fruit may be harvested when they have reached partial or fill ripeness and still have the robustness to withstand handling and transport to reach the consumer in good condition. In this way high quality ripe fruit can be made available to the consumer with reduced requirement for post-harvest treatment. High quality fruit will have improved flavour and texture.

In addition high quality fruit can be produced consistently over a wide harvest period. Such fruit can be held in store for long periods and ripened to optimal quality by the supply of exogenous ethylene.

The invention will now be described further with reference to the accompanying drawings, in which:

EXAMPLE 1

Isolation of banana ACS cDNA clones

The nucleic acid sequences from cloned ACS genes from 6 plant species were compared inorder to identify regions of maximum sequence conservation. Degenerate oligonucleotides based on these conserved regions were designed for use as PCR primers for amplification of ACS gene fragments from banana:

| 5' PRIMER: | | | | | | | | |
|---|---|---|---|---|---|---|---|---|
| Tomato | F | Q | D | Y | H | G | L | (SEQ-ID-NO-3) |
| Tomato | TTT | CAA | GAT | TAT | CAT | GGC | TTG | (SEQ-ID-NO-4) |
| Squash | TTT | CAA | GAT | TAC | CAT | GGC | TTA | (SEQ-ID-NO-5) |
| Mung Bean | TTT | CAG | GAT | TAT | CAT | GGT | CTG | (SEQ-ID-NO-6) |
| Tobacco | TTT | CAA | GAT | TAT | CAC | GGC | CTA | (SEQ-ID-NO-7) |
| Carnation | TTT | CAG | GAT | TAT | CAT | GGT | TTG | (SEQ-ID-NO-8) |
| Moth Orchid | TTT | CAG | GAC | TAT | CAT | GGC | CTC | (SEQ-ID-NO-9) |
| BACCS-2 | 5'-TTT CAR GAY TAY CAY GGY YTG-3' | | | | | | | (SEQ-ID-NO-10) |
| | (R = A or G; Y = T or C) | | | | | | | |
| 3' PRIMER: | | | | | | | | |
| Tomato | P | S | N | P | L | G | T | (SEQ-ID-NO-11) |
| Tomato | CCA | TCA | AAT | CCA | TTG | GGC | ACC | (SEQ-ID-NO-12) |
| Squash | CCC | TCA | AAT | CCC | TTA | GGC | ACA | (SEQ-ID-NO-13) |
| Mung Bean | CCA | TCA | AAT | CCA | TTA | GGC | ACA | (SEQ-ID-NO-14) |
| Tobacco | CCA | TCA | AAT | CCA | TTA | GGC | ACC | (SEQ-ID-NO-15) |
| Moth Orchid | CCT | TCG | AAT | CCT | CTG | GGC | ACC | (SEQ-ID-NO-16) |
| BACCS-4 | 5'-BGT KCC YAR DGG ATT TSA BGG-3' | | | | | | | (SEQ-ID-NO-17) |
| | (B = C or T or G; K = G or T; Y = C or T; | | | | | | | |
| | D = T or G or A; S = G or C) | | | | | | | |

An 800bp fragment was amplified from banana genomic DNA isolated from leaf tissue by PCR using these degenerate primers (Denaturation, 94° C. for 1 min; Annealing, 62° C. for 0.5 min; Extension, 73° C. for 2 min; 35 cycles; End extension 73° C. for 6 min). This PCR product was cloned into a plasmid vector to give the clone pBASH14 which was partially sequenced. 210 bp of sequence was determined at the 5' end of the clone. The encoded amino acid sequence showed significant homology (approx 90%) to tomato ACS genes LEACC1 and LEACC2 surrounding a 134 bp intron:

pBASH14=SEQ-ID-NO-18

TOMACC1=SEQ-ID-NO-20

TOMACC2=SEQ-ID-NO-21

| | | | | | | | | | | | | |
|---|---|---|---|---|---|---|---|---|---|---|---|---|
| pBASH14 | TTTCAGGACTACCATGGTCTGCCGGACTTCCGTAAGTAATCACCGTCTGC | | | | | | | | | | | |
| ID-NO-19 | F | Q | D | Y | H | G | L | P | D | F | R | K   <------------- |
| TOMACC1 | F | Q | D | Y | H | G | L | P | E | F | R | K |
| TOMACC2 | F | Q | D | Y | H | G | L | P | E | F | T | N |
| | * | * | * | * | * | * | * | * | * | | | |
| | ATCCATAATGCAGCTCCTCGATCCTTACGCATGCGTGCCATGAACGATGA | | | | | | | | | | | |
| | ------------------ Intron -------------------------- | | | | | | | | | | | |
| | GGGCACAGTTGGATCGATATGCGTTGCTATAGCCGAAAGTAATGACGCGA | | | | | | | | | | | |
| | ---------------------------------------------------- | | | | | | | | | | | |
| | TCATCTATGGAAATGCACAGGCCATTGCCAAGTTCATGGAGAAAGCGAGA | | | | | | | | | | | |
| ID-NO-22 ------------------> | A | I | A | K | F | M | E | K | A | | | R |
| TOMACC1 (SEQ-ID-NO-23) | A | I | A | K | F | M | E | K | T | | | R |
| TOMACC2 (SEQ-ID-NO-24) | A | I | A | K | F | M | E | K | T | | | R |
| | * | * | * | * | * | * | * | * | | | | * |
| | GGAGGACGAGC | | | | | | | | | | | |
| ID-NO-22 | G | G | R | | | | | | | | | |
| TOMACC1 | G | G | R | | | | | | | | | |
| TOMACC2 | G | G | K | | | | | | | | | |
| | * | * | | | | | | | | | | | pBASH14 was used as a hybridisation probe to screen 400,000 clones of a cDNA library prepared from RNA extracted from ripening bananas. Eight hybridising plaques were identified and purified. Nucleotide sequence analysis showed that clone ACS6 encoded the complete ACS amino acid sequence when compared to ACS genes from other species.

EXAMPLE 2

Isolation of banana EFE cDNA clones

The nucleic acid sequences from cloned EFE genes from 7 plant species were compared inorder to identify regions of maximum sequence conservation. Degenerate oligonucleotides based on these conserved regions were designed for use as PCR primers for amplification of EFE gene fragments from banana:

| 5' PRIMER: | | | | | | | | |
|---|---|---|---|---|---|---|---|---|
| Tomato | D | W | E | S | T | F | F | (SEQ-ID-NO-25) |
| Tomato | GAT | TGG | GAA | AGC | ACT | TTC | TTC | (SEQ-ID-NO-26) |
| Melon | GAC | TGG | GAA | AGC | ACT | TTT | TTT | (SEQ-ID-NO-27) |
| Peach | GAC | TGG | GAA | AGC | ACC | TTC | TAC | (SEQ-ID-NO-28) |
| Avocado | GAC | TGG | GAG | AGC | ACC | TTC | TTC | (SEQ-ID-NO-29) |
| Mustard | GAT | TGG | GAA | AGC | ACT | TTC | TAC | (SEQ-ID-NO-30) |
| Apple | GAC | TGG | GAA | AGC | ACC | TTC | TTC | (SEQ-ID-NO-31) |
| Carnation | GAT | TGG | GAG | AGC | ACC | TTC | TAC | (SEQ-ID-NO-32) |
| BEFE-5 | 5'-GAY TGG GAR AGC ACY TTY T-3' | | | | | | | (SEQ-ID-NO-33) |
| | (Y = T or C; R = A or G) | | | | | | | |
| 3' PRIMER | | | | | | | | |
| Tomato | V | S | N | Y | P | P | C | (SEQ-ID-NO-34) |
| Tomato | GTT | AGC | AAC | TAT | CCA | CCA | TGT | (SEQ-ID-NO-35) |
| Peach | GTT | AGC | AAC | TAC | CCT | CCT | TGT | (SEQ-ID-NO-36) |
| Apple | GTC | AGC | AAC | TAC | CCT | CCA | TGC | (SEQ-ID-NO-37) |
| Avocado | GTC | AGC | AAC | TAC | CCA | CCC | TGC | (SEQ-ID-NO-38) |
| Melon | GTT | AGC | AAT | TAC | CCC | CCA | TGT | (SEQ-ID-NO-39) |
| Mustard | GTG | AGC | AAC | TAT | CCA | GCT | TGT | (SEQ-ID-NO-40) |
| BEFE-2 | 5'-RCA DGG WGG RTA RTT GCT VAC-3' | | | | | | | (SEQ-ID-NO-41) |
| | (R = A or G; D = T or A or G; W = A or T; V = A or C or G) | | | | | | | |

A 330 bp fragment was amplified from banana genomic DNA isolated from leaf tissue by PCR using these degenerate primers (Denaturation, 94° C. for 1 min; Annealing, 59° C. for 0.5 min; Extension, 73° C. for 2 min; 35 cycles; End extension 73° C. for 6 min). This PCR product was cloned into a plasmid vector to give the clone pBEAR13 which was fully sequenced. 210 bp of sequence was determined at the 5' end of the clone. The encoded amino acid sequence showed significant homology (approx 70–80%) to EFE genes from other species surrounding a 89 bp intron:

pBEAR13=SEQ-ID-NO-42

Aco1=SEQ-ID-NO-44

Aco2=SEQ-ID-NO-45

Aco3=SEQ-ID-NO-46

| pBEAR13 | GGGAGAGCACCTTTTTCCTGCGTCATCTCCCCGTCTCCAACATTTCTGAG |
|---|---|
| ID-NO-43 | E S T F F L R H L P V S N I S E |
| Tomato Aco1 | E S T F F L R H L P T S N I S Q |
| Tomato Aco2 | E S T F F L R H L P S S N I S Q |
| Tomato Aco3 | E S T F F L R H L P T S N I S Q |
|  | * * * * * * * * * *   * * * * * |
| pBEAR13 | ATCCCCGATCTTGATGACCAGTATAGGTTGCACGATCTGATCATGATGTC |
|  | I P D L D D Q Y R <- - - - - - - - - - - - - - - - - - - - - - - |
|  | V P D L D E E Y R |
|  | L P D L D D V Y R |
|  | V P D L D E E Y R |
|  | * * * * * * |
| pBEAR13 | ATCTTCTAGCCTTGTCTTTTCACCTTGCTCATCGTTTCGTTTCTTGGGAC |
|  | - - - - - - - - - - - - - - - - - - Intron - - - - - - - - - - - - - - - - - - - - - - - |
| pBEAR13 | GATGACTGCGTGCAGGAAGGCGATGAAGGAATTTGCTGCAGCGATAGAGA |
| ID-NO-47 | - - - - - - - - - - - - - - > K A M K E F A A A I E |
| ID-NO-48 | E V M R D F A K R L E |
| ID-NO-49 | — V M R D F R K R L E |
| ID-NO-50 | E V M R D F A K R L E |
|  | * * |
| pBEAR13 | AGCTGGCAGAGCGGCTGCTCGACTTGCTGGGTGAGAACCTGGAGCTGGAG |
|  | K L A E R L L D L L G E N L E L E |
|  | K L A E E L L D L L C E N L G L E |
|  | K L A E E L L D L L C E N L G L E |
|  | K L A E E L L D L L C E N L G L E |
|  | * * * *   * * * * *   * * *   * * |
| pBEAR13 | AAGGGGCTCCTGAAGAAGGCCTTCTCTAATGGATCCAAGGGGCCAACCTT |
|  | K G L L K K A F S N G S K G P T F |
|  | K G Y L K N A F — Y G S K G P N F |
|  | K S Y L K N T F — Y G S K G P N F |
|  | K G Y L K N A F — Y G S K G P N F |
|  | *     * * * *         * * * * *   * |
| pBEAR13 | TGGGACCAAGGTCAGCAACTACCCACCTTGC |
|  | G T K V S N Y P P C |
|  | G T K V S N Y P P C |
|  | G T K V S N Y P P C |
|  | G T K V S N Y P P C |
|  | * * * * * * * * * * | pBEAR13 was used as a hybridisation probe to screen 400,000 clones of a cDNA library prepared from RNA extracted from ripening bananas. 1200 hybridising plaques were identified. Nucleotide sequence analysis showed that clone ACOS7 encoded the complete EFE amino acid sequence when compared to EFE genes from other species.

EXAMPLE 3

Construction of ACS partial-sense vectors with a constitutive promoter.

A vector is constructed using sequences corresponding to a fragment of the insert of a banana ACS cDNA (isolated as shown in example 1). This fragment is synthesised by polymerase chain reaction using synthetic primers. The ends of the fragment are made flush with T4 polymerase and it is cloned into the vector pJR1 (Smith et al, 1988, Nature, 334:724–726) which has previously been cut with SmaI. pJR1 is a Bin19 (Bevan 1984, Nucleic Acids Research, 12:8711–872 1) based vector which permits the expression of the ACO partial-sense RNA under the control of the CAMV 35S promoter. This vector includes a nopaline synthase (nos) 3' end termination sequence.

EXAMPLE 4

Construction of EFE partial-sense constructs with a constitutive promoter.

A vector is constructed using sequences corresponding to a fragment of the insert of a banana ACO cDNA (isolated as shown in example 2). This fragment is synthesised by polymerase chain reaction using synthetic primers. The ends of the fragment are made flush with T4 polymerase and it is cloned into the vector pJR1 (Smith et al, 1988, Nature, 334:724–726) which has previously been cut with SmaI. pJR1 is a Bin19 (Bevan 1984, Nucleic Acids Research, 12:8711–8721) based vector which permits the expression of the ACO partial-sense RNA under the control of the CAMV 35S promoter. This vector includes a nopaline synthase (nos) 3' end termination sequence.

EXAMPLE 5

Generation of transformed banana plants

Vectors are transferred to *Agrobacterium tumefaciens* LBA4404 (a micro-organism widely available to plant biotechnologists) and are used to transform banana plants. Transformation of banana meristems follow the protocols described by May et al (1995, Biotechnology 13:486–492). Transformed plants are identified by their ability to grow on media containing the antibiotic kanamycin. Plants are regenerated and grown to maturity. Ripening fruit are analysed for modifications to their fruit ripening characteristics.

We claim:

1. An isolated DNA molecule encoding 1-aminocyclopropane-1-carboxylic acid synthase (ACS) consisting of the sequence SEQ ID NO:1.

2. An isolated DNA molecule encoding an ethylene-forming enzyme (EFE) consisting of the nucleotide sequence SEQ ED NO:2.

3. A DNA construct comprising a DNA sequence as claimed in claim 1 or claim 2 preceded by a transcriptional initiation region operative in plants, so that the construct can generate RNA in plant cells.

4. A vector for the genetic transformation of plant cells comprising a DNA construct having upstream promoter and downstream termination signals and therebetween a DNA sequence as claimed in claim 1 or claim 2 in sense or antisense configuration.

* * * * *